United States Patent
Fujiwara et al.

(10) Patent No.: US 9,212,288 B2
(45) Date of Patent: *Dec. 15, 2015

(54) GLASS FLAKE AND COATED GLASS FLAKE

(75) Inventors: Kosuke Fujiwara, Tokyo (JP); Akihiro Koyama, Tokyo (JP)

(73) Assignee: NIPPON SHEET GLASS COMPANY, LIMITED, Tokyo (JP)

( * ) Notice: Subject to any disclaimer, the term of this patent is extended or adjusted under 35 U.S.C. 154(b) by 262 days.

This patent is subject to a terminal disclaimer.

(21) Appl. No.: 12/993,058

(22) PCT Filed: May 28, 2009

(86) PCT No.: PCT/JP2009/059766
§ 371 (c)(1),
(2), (4) Date: Nov. 16, 2010

(87) PCT Pub. No.: WO2009/154064
PCT Pub. Date: Dec. 23, 2009

(65) Prior Publication Data
US 2011/0064951 A1 Mar. 17, 2011

(30) Foreign Application Priority Data

Jun. 18, 2008 (JP) .................................. 2008-159195
Aug. 27, 2008 (JP) .................................. 2008-217728

(51) Int. Cl.
*B32B 17/00* (2006.01)
*C03C 3/087* (2006.01)
(Continued)

(52) U.S. Cl.
CPC ............... *C09D 11/00* (2013.01); *A61K 8/0258* (2013.01); *A61K 8/26* (2013.01); *A61Q 1/02* (2013.01); *C03B 37/005* (2013.01); *C03C 3/087* (2013.01);
(Continued)

(58) Field of Classification Search
None
See application file for complete search history.

(56) References Cited

U.S. PATENT DOCUMENTS 6,313,052 B1  11/2001  Nakashima et al.
7,166,549 B2 *  1/2007  Fechner et al. ............... 501/56
(Continued)

FOREIGN PATENT DOCUMENTS

EP  1 083 155 A1  3/2001
EP  1865031 A1  12/2007
(Continued)

OTHER PUBLICATIONS

Machine Translation of JP 2001-213639 (2001).*
(Continued)

*Primary Examiner* — Alexandre Ferre
(74) *Attorney, Agent, or Firm* — Seager, Tufte & Wickhem LLP

(57) ABSTRACT

Disclosed is a glass flake (10) having improved heat resistance and improved chemical durability, which is composed of a glass base material satisfying, as expressed in mass %, $60 \leq SiO_2 \leq 70$, $5 \leq Al_2O_3 \leq 15$, $1 \leq MgO \leq 10$, $10 \leq CaO \leq 25$ and $4 < (Li_2O + Na_2O + K_2O) < 9$. The temperature difference $\Delta T$ obtained by taking the devitrification temperature of the glass base material from the working temperature thereof is preferably within the range of 0-200° C. The glass transition temperature of the glass base material is preferably within the range of 560-750° C. It is desirable that the value of $\Delta W$, which serves as an index for the acid resistance of the glass base material, is within the range of 0.05-1.2 mass %.

9 Claims, 4 Drawing Sheets

(51) Int. Cl.

| | |
|---|---|
| *C03C 3/091* | (2006.01) |
| *C03C 6/04* | (2006.01) |
| *C03B 37/005* | (2006.01) |
| *C09D 11/00* | (2014.01) |
| *A61K 8/02* | (2006.01) |
| *A61K 8/26* | (2006.01) |
| *A61Q 1/02* | (2006.01) |
| *C03C 12/00* | (2006.01) |
| *C03C 17/00* | (2006.01) |
| *C09C 1/00* | (2006.01) |

(52) U.S. Cl.
CPC ............... *C03C 3/091* (2013.01); *C03C 12/00* (2013.01); *C03C 17/00* (2013.01); *C09C 1/0018* (2013.01); *C09C 1/0021* (2013.01); *A61K 2800/436* (2013.01); *A61K 2800/621* (2013.01); *C03C 2217/72* (2013.01); *C09C 2200/102* (2013.01); *Y10T 428/2996* (2015.01)

(56) References Cited

U.S. PATENT DOCUMENTS

| | | | |
|---|---|---|---|
| 2002/0011080 A1* | 1/2002 | Naka et al. .................. 65/66 |
| 2004/0152579 A1 | 8/2004 | Ishiki et al. | |
| 2005/0049133 A1 | 3/2005 | Fujiwara et al. | |
| 2006/0048679 A1 | 3/2006 | Fujiwara et al. | |
| 2008/0124559 A1 | 5/2008 | Fujiwara et al. | |
| 2010/0183737 A1* | 7/2010 | Fujiwara et al. .............. 424/613 |

FOREIGN PATENT DOCUMENTS

| | | | |
|---|---|---|---|
| JP | 3040938 A | | 2/1991 |
| JP | 10-297930 A | | 11/1998 |
| JP | 11-240734 A | | 9/1999 |
| JP | 11-310429 A | | 11/1999 |
| JP | 11-310432 A | | 11/1999 |
| JP | 11-314933 A | | 11/1999 |
| JP | 2001-080935 A | | 3/2001 |
| JP | 2001-213639 A | | 8/2001 |
| JP | 2001213639 A | * | 8/2001 |
| JP | 2003020291 A | | 1/2003 |
| JP | 2005097080 A | | 4/2005 |
| JP | 2007-145699 A | | 6/2007 |
| JP | 2007-145700 A | | 6/2007 |
| JP | 10198028 A | | 9/2010 |
| WO | 2006/068255 A1 | | 6/2006 |
| WO | WO 2007148758 A1 | * | 12/2007 |

OTHER PUBLICATIONS

"PCT International Preliminary Report on Patentability for International Application No. PCT/JP2009/059766," with an International Filing Date of May 28, 2009, as completed by an Authorized Officer of the IPEA/JP. 4 pages.

Peng Wei, "Process for Producing Flake Glass", Glass (a Chinese Academic Journal), vol. 23, I, pp. 41-45. Translation of the Related Part of D2.

Chinese Application No. 200980118510.6, filed May 28, 2009, Chinese Patent Office, First Office Action dated Mar. 31, 2012.

* cited by examiner

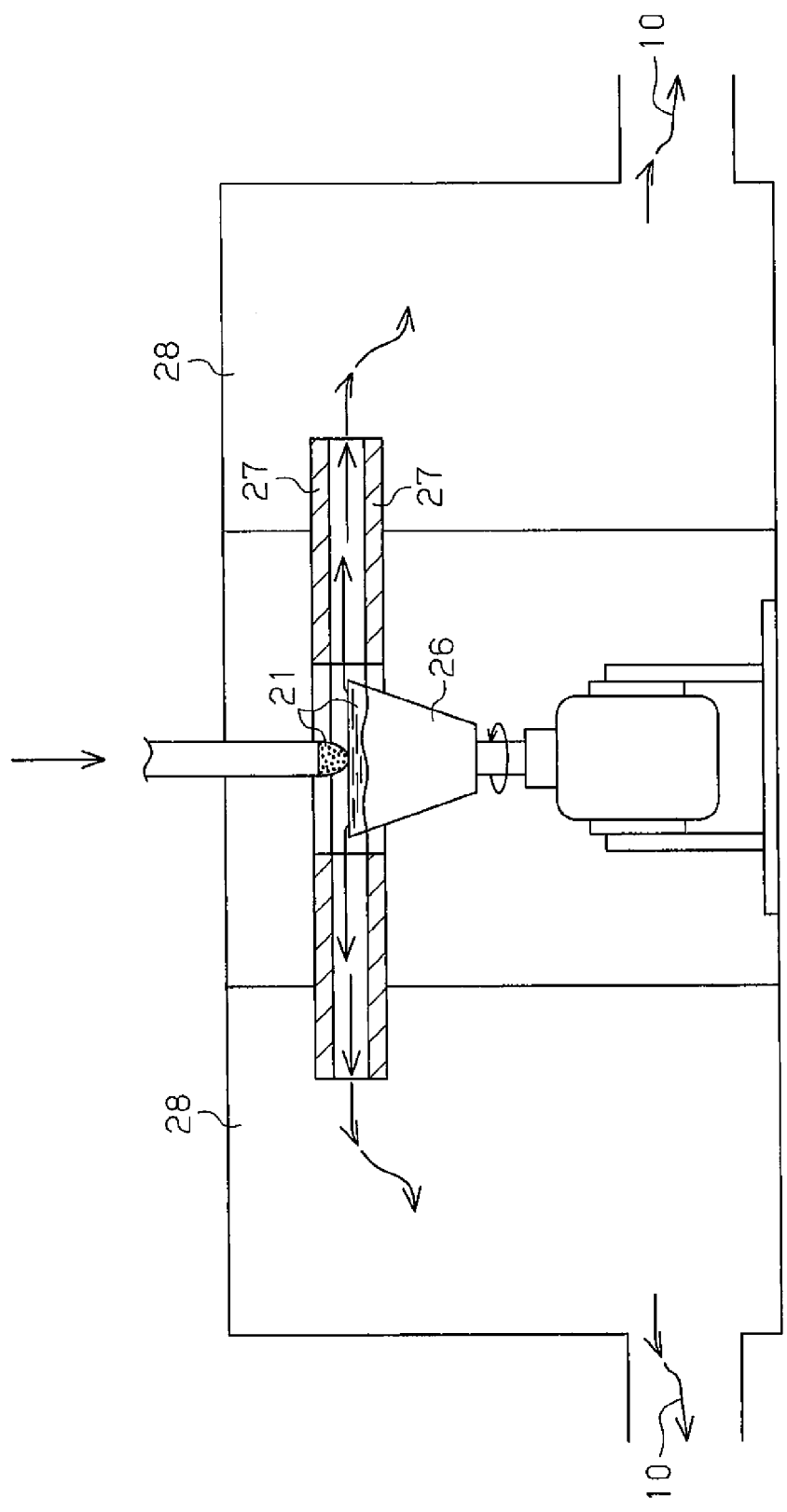

GLASS FLAKE AND COATED GLASS FLAKE

TECHNICAL FIELD

The present invention relates to glass flakes and coated glass flake blended with, for example, resin compositions, paint, ink, cosmetics, and the like to obtain superior color tones and luster.

BACKGROUND ART

When such glass flakes are dispersed in, for example, a resin composition (resin matrix), a resin mold product obtained from the resin composition will have increased strength and dimensional accuracy. Further, glass flakes are blended with paint as lining and applied to metal or a concrete surface. The glass flakes have a metallic color produced by coating their surfaces with a metal. Further, the surfaces of the glass flakes may be coated by a metal oxide to have an interference color resulting from interference of reflection light. In this manner, glass flakes coated by a metal coating or a metal oxide coating is preferable for use as a luster pigment. Luster pigment using such glass flakes is preferably used for applications in which the color tone and luster are important, such as paint and cosmetics.

A glass flake is fabricated by inflating a molten glass base material with an injection nozzle to form a balloon-shaped hollow glass film and then crushing the hollow glass film with a pressing roller, for example. When such a fabrication process is taken into account, it is required that glass flakes have superior meltability, satisfactory formability, a suitable temperature-viscosity property, and a devitrification temperature that is lower than the working temperature. The working temperature is the temperature when the viscosity of glass is 100 Pa·s (1000 P). Further, the devitrification temperature is the temperature at which crystals form and start to grow in the molten glass base material.

For the temperature-viscosity property, it is preferable that the working temperature be less than or equal to 1300° C. since the glass flakes become difficult to form, particularly, when the working temperature becomes too high. A lower working temperature for glass decreases the cost of fuel when melting the glass crude material. This also decrease the thermal damage caused to a kiln or fabrication apparatus of the glass flakes and thereby allows for the kiln or fabrication apparatus to have a longer life.

Further, when forming a metal coating or a metal oxide coating on glass flakes, the glass flakes may undergo a high-temperature treatment. Additionally, glass flakes or coated glass flakes may be blended with paint and undergo a high-temperature treatment for applications such as baking finishing. Accordingly, glass flakes require sufficient heat resistance. Soda-lime glass, which is typically used as a so-called sheet glass composition, includes a large amount of alkali metal oxide and does not have sufficient heat resistance. When considering the application of glass flakes blended with paint or cosmetics, a coating film or coating would require acid resistance, alkali resistance, and the like. Hence, the glass flakes would require high chemical durability.

To meet these requirements, the applicant of the present application has suggested glass flakes that will now be described. For example, patent document 1 suggests glass flakes that specify the content of silicon dioxide ($SiO_2$), the total content of silicon dioxide and aluminum oxide ($Al_2O_3$), the total content of magnesium oxide (MgO) and calcium oxide (CaO), and the total content of lithium oxide ($Li_2O$), sodium oxide ($Na_2O$), and potassium oxide ($K_2O$).

Patent document 2 suggests glass flakes that specify the total content of oxide magnesium and calcium oxide, the total content of lithium oxide and sodium oxide, and the content of titanium dioxide ($TiO_2$).

PRIOR ART DOCUMENTS

Patent Document 1: Japanese Laid-Open Patent Publication NO. 2007-145699
Patent Document 2: Japanese Laid-Open Patent Publication No. 2007-145700

DISCLOSURE OF THE INVENTION

Problems that are to be Solved by the Invention

Silicon dioxide and aluminum oxide are components used to form the skeleton for glass. When the content of silicon dioxide and aluminum oxide are insufficient, the glass transition temperature does not become high, and the heat resistance is insufficient. Further, silicon dioxide has a tendency to increase acid resistance, while aluminum oxide has a tendency to decrease acid resistance. Thus, the balance of silicon dioxide and aluminum oxide is important. Magnesium oxide and calcium oxide are components that adjust the devitrification temperature and viscosity of glass in a satisfactory manner.

However, patent documents 1 and 2 disclose that the content of aluminum oxide is preferably 5% or less. In the described examples, the content of aluminum oxide is 3.20 percent by mass or less in patent document 1 and 4.84 percent by mass or less in patent document 2. In patent documents 1 and 2, the content of silicon dioxide is set to be excessive in comparison with the content of aluminum oxide. Thus, the glass flakes have insufficient heat resistance. Further, chemical durability, such as water resistance, is also decreased.

In addition, in the glass flakes described in each of patent documents 1 and 2, the total content of oxide lithium, sodium oxide, and potassium oxide ($Li_2O+Na_2O+K_2O$) is 13 percent by mass or greater. However, when the content of ($Li_2O+Na_2O+K_2O$) is 13 percent by mass or greater, particularly, when the content of $Na_2O$ is large, the glass flakes would have insufficient heat resistance.

It is an object of the present invention to provide glass flakes and coated glass flakes that have improved heat resistance and chemical durability.

Means for Solving the Problems

The inventors of the present invention have conducted studies on a preferable glass composition for glass flakes to achieve the above object. Based on the result of the studies, the inventors have found that glass flakes having improved heat resistance, chemical durability (in particular, acid resistance), and formability are obtained by controlling the contents of silicon dioxide ($SiO_2$) and aluminum oxide ($Al_2O_3$) and by controlling the total content of alkali metal oxides ($Li_2O+Na_2O+K_2O$) and conceived the present invention.

Specifically, a first aspect of the present invention is a glass flake being characterized in that:
the glass flake is formed from a glass base material of which the composition when indicated by percent by mass;
$60 \leq SiO_2 \leq 70$
$5 \leq Al_2O_3 \leq 15$,
$1 \leq MgO \leq 10$,
$10 \leq CaO \leq 25$, and
$4 < (Li_2O+Na_2O+K_2O) < 9$.

In one example, a temperature difference ΔT obtained by subtracting a devitrification temperature from a working temperature of the glass base material is 0° C. to 200° C.

In one example, a glass transition temperature of the glass base material is 560° C. to 750° C.

In one example, ΔW, which is an index for acid resistance of the glass base material, is 0.05 to 1.2 percent by mass.

A coated glass flake according to one aspect of the present invention includes the glass flake according to the first aspect and a coating having a main component of metal or metal oxide that covers a surface of the glass flake.

The glass base material forming the glass flake according to the first aspect of the present invention is set to satisfy $60 \leq SiO_2 \leq 70$ and $5 \leq Al_2O_3 \leq 15$. This obtains sufficient contents of silicon dioxide and aluminum oxide, and the silicon dioxide and aluminum oxide sufficiently function to form a skeleton for glass. Further, the glass transition temperature is high, the meltability is satisfactory, and the acid resistance and water resistance are increased. Further, the contents of magnesium oxide and calcium oxide are set to be $1 \leq MgO \leq 10$ and $10 \leq CaO \leq 25$. This obtains a satisfactory devitrification temperature and viscosity during glass formation, while maintaining the heat resistance of glass. In addition, the total amount of lithium oxide, sodium oxide, and potassium oxide is set to be $4 < (Li_2O + Na_2O + K_2O) < 9$. In this manner, the contents of alkali metal oxides are sufficient. Thus, the devitrification temperature and viscosity during glass formation are satisfactory. The glass base material having the above composition increases the heat resistance and chemical durability of the glass flake.

When the temperature difference ΔT obtained by subtracting a devitrification temperature from a working temperature of the glass base material is 0° C. to 200° C., devitrification is suppressed during glass formation and further homogeneous glass flakes may be obtained.

When the glass transition temperature of the glass base material is 560° C. to 750° C., the heat resistance of the glass flake is increased.

When ΔW, which is an index for acid resistance of the glass base material, is 0.05 to 1.2 percent by mass, the acid resistance of the glass flake is increased.

A coated glass, which includes a coating having a main component of metal or metal oxide that covers the surface of the glass flake, allows the coating to have a metallic color, an interference color, or the like.

BRIEF DESCRIPTION OF THE DRAWINGS

FIG. 5 is a cross-sectional view showing another apparatus for fabricating the glass flakes.

DESCRIPTION OF EMBODIMENTS

One embodiment will now be discussed in detail with reference to the drawings:

In this specification, a numerical value indicating a composition will be expressed as percent by mass. The composition of a glass base material for fabricating glass flakes of the present embodiment will be set as shown below, expressed in percent by mass:

$60 \leq SiO_2 \leq 70$,
$5 \leq Al_2O_3 \leq 15$,
$1 \leq MgO \leq 10$,
$10 \leq CaO \leq 25$, and
$4 < (Li_2O + Na_2O + K_2O) < 9$.

In this specification, $SiO_2$ refers to silicon dioxide (silica), $Al_2O_3$ refers to aluminum oxide (alumina), MgO refers to magnesium oxide, CaO refer to calcium oxide, $Li_2O$ refers to lithium oxide, $Na_2O$ refers to sodium oxide, and $K_2O$ refers to potassium oxide.

Figure 1:
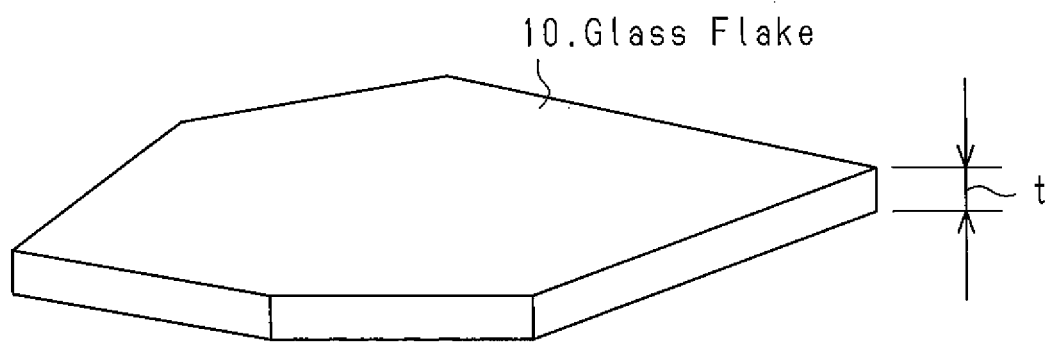
FIG. 1(a) is a schematic perspective view showing a glass flake in one embodiment.
FIG. 1(B) is a plan view showing the glass flake.
Figure 1:
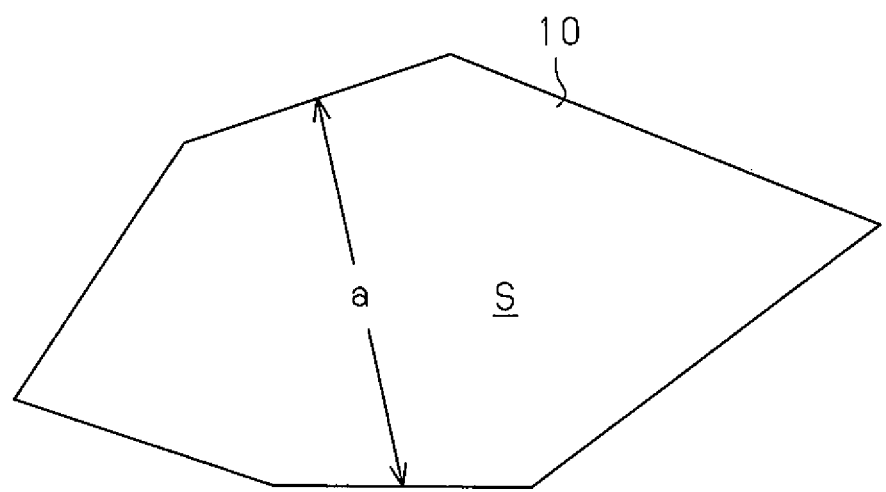

FIG. 1(a) is a perspective view showing a glass flake 10, and FIG. 1(b) is a plan view showing the glass flake 10. Referring to FIG. 1(a), the glass flake 10 has an average thickness t of 0.1 to 15 μm. Further, the glass flake 10 has an aspect ratio (average grain diameter a/average thickness t) of 2 to 1000. Accordingly, the glass flake 10 is a thin grain. The glass flake 10 may have a planar shape that is hexagonal as shown in FIG. 1(a), pentagonal, octagonal, and so on. In this specification, when viewed from above as shown in FIG. 1(b), the average grain diameter "a" is defined as the square root of the area S of the glass flake 10 ($a = S^{1/2}$).

Next, the composition of the glass flake 10, the fabrication method of the glass flake 10, the physical properties of the glass flake 10, a coated glass flake, and applications (resin composition, paint, ink composition, and cosmetics) will be sequentially described.

Composition of Glass Flake 10

($SiO_2$)

Silicon dioxide ($SiO_2$) is a main component that forms a skeleton for the glass flake 10. In this specification, the main component refers to the component corresponding to the largest content. Further, $SiO_2$ is a component that adjusts the devitrification temperature and viscosity when forming glass while maintaining the heat resistance of the glass. When the content of $SiO_2$ is less than 60 percent by mass, the devitrification temperature rises too much. This makes it difficult to fabricate the glass flake 10 and decreases the acid resistance of the glass flake 10. When the content of $SiO_2$ exceeds 70 percent by mass, the melting point of glass becomes too high and it becomes difficult to uniformly melt the crude material.

Accordingly, the lower limit for $SiO_2$ is 60 percent by mass or greater, preferably 63 percent by mass or greater, more preferably 64 percent by mass or greater, and most preferably greater than 65 percent by mass. The upper limit for $SiO_2$ is 70 percent by mass or less, preferably 69 percent by mass or less, more preferably 68 percent by mass or less, and most preferably 67 percent by mass or less. Thus, the range for the content of $SiO_2$ is selected from any combination of these upper and lower limits and is, for example, preferably 63 to 68 percent by mass.

($B_2O_3$)

Diboron Trioxide ($B_2O_3$) is a Component that Forms the skeleton for glass and is a component that adjusts the devitrification temperature and viscosity when forming the glass. The content of $B_2O_3$ is preferably $0 \leq B_2O_3 \leq 6$. When the content of $B_2O_3$ exceeds 6 percent by mass, this corrodes the furnace wall of a melting kiln or heat storage kiln and greatly shortens the life of the kiln. Accordingly, the upper limit of $B_2O_3$ is preferably 6 percent by mass or less, more preferably less than 2 percent by mass, and even more preferably less than 1 percent by mass. Most preferably, $B_2O_3$ is substantially not contained.

($Al_2O_3$)

Aluminum oxide ($Al_2O_3$) is a component that forms a skeleton for the glass flake 10 and is a component that adjusts the devitrification temperature and viscosity of glass when forming glass while maintaining the heat resistance. Further, $Al_2O_3$ is a component that increases the water resistance, while decreasing the acid resistance. When $Al_2O_3$ is less than 5 percent by mass, the devitrification temperature and viscosity cannot be sufficiently adjusted. Otherwise, the water resistance cannot be sufficiently improved. When the content of $Al_2O_3$ exceeds 15 percent by mass, the melting point of glass becomes too high, uniform melting of the glass becomes difficult, and the acid resistance decreases. Accordingly, the lower limit of $Al_2O_3$ is 5 percent by mass or greater, preferably 6 percent by mass or greater, more preferably 8 percent by mass or greater, and most preferably 10 percent by mass or greater. The upper limit of $Al_2O_3$ is 15 percent by mass or less, preferably 13 percent by mass or less, and most preferably less than 12 percent by mass. Thus, the range for the content of $Al_2O_3$ is selected from any combination of these upper and lower limits and is, for example, preferably 8 to 13 percent by mass.

(MgO, CaO)

Magnesium oxide (MgO) and calcium oxide (CaO) are components that adjust the devitrification temperature and viscosity when forming glass, while maintaining the heat resistance of glass. The content of MgO is $1 \leq MgO \leq 10$. When the content of MgO is less than 1 percent by mass, the effect for adjusting the devitrification temperature and viscosity is not sufficient. When the content of MgO exceeds 10 percent by mass, the devitrification temperature rises too much, and it becomes difficult to fabricate the glass flake 10. Accordingly, the lower limit of MgO is 1 percent by mass or greater and preferably 2 percent by mass or greater. The upper limit of MgO is 10 percent by mass or less, preferably 8 percent by mass or less, more preferably 5 percent by mass or less, and most preferably 4 percent by mass or less. Thus, the range for the content of MgO is selected from any combination of these upper and lower limits and is, for example, preferably 2 to 5 percent by mass.

The content of CaO is $10 \leq CaO \leq 25$. When the content of CaO is less than 10 percent by mass, the effect for adjusting the devitrification temperature and viscosity is not sufficient. When the content of CaO exceeds 25 percent by mass, the devitrification temperature rises too much, and it becomes difficult to fabricate the glass flake 10. Accordingly, the lower limit of CaO is 10 percent by mass or greater, preferably 12 percent by mass or greater, more preferably 14 percent by mass or greater, and most preferably greater than 15 percent by mass. The upper limit of CaO is 25 percent by mass or less, preferably 23 percent by mass or less, more preferably 21 percent by mass or less, and most preferably 20 percent by mass or less. Thus, the range for the content of CaO is selected from any combination of these upper and lower limits and is, for example, preferably 12 to 21 percent by mass.

(SrO)

Strontium oxide (SrO) is a component that adjusts the devitrification temperature and viscosity when forming glass. SrO is also a component that decreases the acid resistance of glass. SrO is not essential but may be used as a component that adjusts the devitrification temperature and viscosity when forming glass. However, when the content of SrO exceeds 10 percent by mass, the acid resistance decreases. Accordingly, the upper limit of SrO is preferably 10 percent by mass or less, more preferably 5 percent by mass or less, and even more preferably 2 percent by mass or less. Most preferably, SrO is substantially not contained.

(BaO)

Barium oxide (BaO) is a component that adjusts the devitrification temperature and viscosity when forming glass. BaO is also a component that decreases the acid resistance of glass. BaO is not essential but may be used as a component that adjusts the devitrification temperature and viscosity when forming glass. However, when the content of BaO exceeds 10 percent by mass, the acid resistance decreases. Accordingly, the upper limit of BaO is preferably 10 percent by mass or less, more preferably 5 percent by mass or less, and even more preferably 2 percent by mass or less. Most preferably, BaO is substantially not contained.

(ZnO)

Zinc oxide (ZnO) is a component that adjusts the devitrification temperature and viscosity when forming glass. ZnO easily evaporates and may thus scatter when it is molten. When the content of ZnO exceeds 10 percent by mass, variation in the component ratio resulting from the evaporation becomes prominent, and management of the content in glass becomes difficult. Accordingly, the upper limit of ZnO is preferably 10 percent by mass or less, more preferably 5 percent by mass or less, and even more preferably 2 percent by mass or less. Most preferably, ZnO is substantially not contained.

($Li_2O$, $Na_2O$, $K_2O$)

Alkali metal oxides ($Li_2O$, $Na_2O$, and $K_2O$) are components that adjust the devitrification temperature and viscosity when forming glass. The total content of alkali metal oxides ($Li_2O+Na_2O+K_2O$) is $4<(Li_2O+Na_2O+K_2O)<9$. When ($Li_2O+Na_2O+K_2O$) is 4 percent by mass or less, the melting point of glass becomes too high and it becomes difficult to uniformly melt the crude material. The fabrication of the glass flake 10 also becomes difficult. When ($Li_2O+Na_2O+K_2O$) is 9 percent by mass or greater, the glass transition temperature becomes low, and the heat resistance of glass decreases. Accordingly, the lower limit of ($Li_2O+Na_2O+K_2O$) is greater than 4 percent by mass, preferably 4.5 percent by mass or greater, and more preferably 5 percent by mass or greater. The upper limit of ($Li_2O+Na_2O+K_2O$) is less than 9 percent by mass, preferably 8.5 percent by mass or less, and more preferably 8 percent by mass or less. The range of ($Li_2O+Na_2O+K_2O$) is selected from any combination of these upper and lower limits and is, for example, preferably 4.5 to 8.5 percent by mass.

Lithium oxide ($Li_2O$) is not essential but it is desirable that it be used as a component for adjusting the devitrification temperature and viscosity when forming glass. Further, since $Li_2O$ has an effect for lowering the melting point of glass, the glass crude material easily and uniformly melts when containing it. Further, $Li_2O$ has an effect for lowering the working temperature. This results in easy fabrication of the glass flake 10. However, when the content of $Li_2O$ exceeds 5 percent by mass, the glass transition temperature becomes low, and the heat resistance of glass decreases. Moreover, the working temperature becomes too low relative to the devitrification temperature, and the fabrication of the glass flake 10 becomes difficult. Accordingly, the lower limit of $Li_2O$ is preferably 0 percent by mass or greater, more preferably 0.1 percent by mass or greater, even more preferably 0.5 percent by mass or greater, and most preferably 1 percent by mass or greater. The upper limit of $Li_2O$ is preferably 5 percent by mass or less, more preferably 4 percent by mass or less, even more preferably less than 3 percent by mass, and most preferably less than 2 percent by mass. The range of $Li_2O$ is selected from any combination of these upper and lower limits and is, for example, preferably 0.5 to 3 percent by mass.

Sodium oxide ($Na_2O$) is not essential but it is desirable that it be used as a component for adjusting the devitrification temperature and viscosity when forming glass. However, when the upper limit of the content of $Na_2O$ is 9 percent by mass or greater, the glass transition temperature becomes low, and the heat resistance of glass decreases. Accordingly, the lower limit of $Na_2O$ is preferably 0 percent by mass or greater, more preferably 1 percent by mass or greater, even more preferably greater than 2 percent by mass, and most preferably greater than 3 percent by mass. The upper limit of $Na_2O$ is preferably less than 9 percent by mass, more preferably 8 percent by mass or less, and even more preferably 7 percent by mass or less. The range of $Na_2O$ is selected from any combination of these upper and lower limits and is, for example, preferably 1 to 8 percent by mass.

Potassium oxide ($K_2O$) is not essential but it is desirable that it be used as a component for adjusting the devitrification temperature and viscosity when forming glass. However, when the content of $K_2O$ exceeds 5 percent by mass, the glass transition temperature becomes low, and the heat resistance of glass decreases. Accordingly, the lower limit of $K_2O$ is preferably 0 percent by mass or greater and more preferably 0.1 percent by mass or greater. The upper limit of $K_2O$ is preferably 5 percent by mass or less, more preferably 4 percent by mass or less, even more preferably 3 percent by mass or less, and most preferably less than 2 percent by mass. The content of $K_2O$ is selected from any combination of these upper and lower limits and is, for example, 0 to 4 percent by mass.

($TiO_2$)

Titanium oxide ($TiO_2$) is a component that increases the meltability of glass and the chemical durability and ultraviolet absorptivity of the glass flake 10. Although $TiO_2$ is not an essential component, it is preferable that $TiO_2$ be contained as a component that adjusts the meltability of glass and the chemical durability and optical property of the glass flake 10. However, when the content of $TiO_2$ exceeds 5 percent by mass, the devitrification temperature rises too much and fabrication of the glass flake 10 becomes difficult. Accordingly, the lower limit of $TiO_2$ is preferably 0 percent by mass or greater and more preferably 0.1 percent by mass or greater. The upper limit of $TiO_2$ is preferably 5 percent by mass or less, more preferably 2 percent by mass or less, and even more preferably less than 1 percent by mass.

($ZrO_2$)

Zirconium dioxide ($ZrO_2$) is a component that adjusts the devitrification temperature and viscosity when forming glass. Further, $ZrO_2$ functions to increase the speed of devitrification growth for glass. However, when the content of $ZrO_2$ exceeds 5 percent by mass, the devitrification temperature rises too much and fabrication of the glass flake 10 becomes difficult. Accordingly, the upper limit of $ZrO_2$ is preferably 5 percent by mass or less, more preferably 2 percent by mass or less, and even more preferably 1 percent by mass or less. It is most preferable that $ZrO_2$ be substantially not contained.

(Fe)

Iron (Fe) normally exists in glass in the state of $Fe^{3+}$ or $Fe^{2+}$. $Fe^{3+}$ is a component that increases the ultraviolet absorptivity of glass, and $Fe^{2+}$ is a component that increases the heat-ray absorptivity of glass. Although iron (Fe) is not an essential component, it is preferable that iron (Fe) be contained as a component that adjusts the optical property of the glass flake 10. Further, even when not intended to be contained, iron (Fe) from other industrial crude materials may become inevitably mixed therein. When the content of iron (Fe) increases, coloring of the glass flake 10 becomes prominent. Such coloring is not preferable for applications in which the color tone and luster are important. Accordingly, the upper limit of iron (Fe) in $Fe_2O_3$ equivalent is preferably 5 percent by mass or less, more preferably 2 percent by mass or less, even more preferably 0.5 percent by mass or less, and in particular preferably 0.1 percent by mass or less. It is most preferable that iron (Fe) be substantially not contained.

($SO_3$)

Although sulfur trioxide ($SO_3$) is not an Essential component, it may be contained as a fining agent. When using sulfate crude material, sulfur trioxide may be contained with a content of 0.5 percent by mass or less.

(F)

Fluorine (F) easily evaporates and may thus scatter when it is molten. Further, management of the content in glass is difficult. Accordingly, it is preferable that F be substantially not contained.

($SiO_2$—$Al_2O_3$)

When it is significant that the glass flake 10 has acid resistance, the difference ($SiO_2$—$Al_2O_3$) between the content of $SiO_2$, which increases the acid resistance of the glass flake 10, and the content of $Al_2O_3$, which decreases the acid resistance, is important. The difference is preferably $50 \leq (SiO_2$—$Al_2O_3) \leq 60$. When ($SiO_2$—$Al_2O_3$) is less than 50 percent by mass, the acid resistance of the glass flake 10 becomes insufficient. When ($SiO_2$—$Al_2O_3$) exceeds 60 percent by mass, the devitrification temperature rises too much, and fabrication of the glass flake 10 becomes difficult. Accordingly, the lower limit for the content of ($SiO_2$—$Al_2O_3$) is preferably 50 percent by mass or greater, more preferably 51 percent by mass or greater, even more preferably 52 percent by mass or greater, and most preferably greater than 53 percent by mass. The upper limit for ($SiO_2$—$Al_2O_3$) is preferably 60 percent by mass or less, more preferably 59 percent by mass or less, even more preferably 58 percent by mass or less, and most preferably 57 percent by mass of less. The range for the content of ($SiO_2$—$Al_2O_3$) is selected from any combination of these upper and lower limits and is, for example, 51 to 59 percent by mass.

(MgO+CaO)

When it is significant that the glass flake 10 be easy to fabricate, the sum (MgO+CaO) of the contents is important of MgO and CaO, which are components for adjusting the devitrification temperature and viscosity when forming glass. The sum is preferably within $11 \leq (MgO+CaO) \leq 35$. When (MgO+CaO) is less than 11 percent by mass, the acid resistance of the glass flake 10 becomes insufficient. When the content of (MgO+CaO) exceeds 35 percent by mass, the devitrification temperature rises too much, and fabrication of the glass flake 10 becomes difficult. Accordingly, the lower limit for the content of (MgO+CaO) is preferably 11 percent by mass or greater, more preferably 13 percent by mass or greater, even more preferably greater than 14 percent by mass, in particular preferably 15 percent by mass or greater, and most preferably greater than 17 percent by mass. The upper limit for (MgO+CaO) is preferably 35 percent by mass or less, more preferably 30 percent by mass or less, even more preferably 26 percent by mass or less, and most preferably 24 percent by mass or less. The range for the content of (MgO+CaO) is selected from any combination of these upper and lower limits and is, for example, 13 to 30 percent by mass.

In the present embodiment, when a substance is substantially not contained, this would mean that the substance is intentionally not contained although industrial crude materials, for example, may become inevitably mixed therein. More specifically, such a phrase would refer to a content that is less than 0.1 percent by mass.

As described above in detail, the glass base material for fabricating the glass flake 10 in the present embodiment contains the essential components of $SiO_2$, $Al_2O_3$, MgO, and CaO. The glass base material further contains at least one selected from the group consisting of $Li_2O$, $Na_2O$, and $K_2O$. When necessary, the glass base material may also contain $B_2O_3$, SrO, BaO, ZnO, $TiO_2$, $ZrO_2$, iron oxide (FeO or $Fe_2O_3$), $SO_3$, and the like.

Process for Fabricating Glass Flake 10

Figure 4:
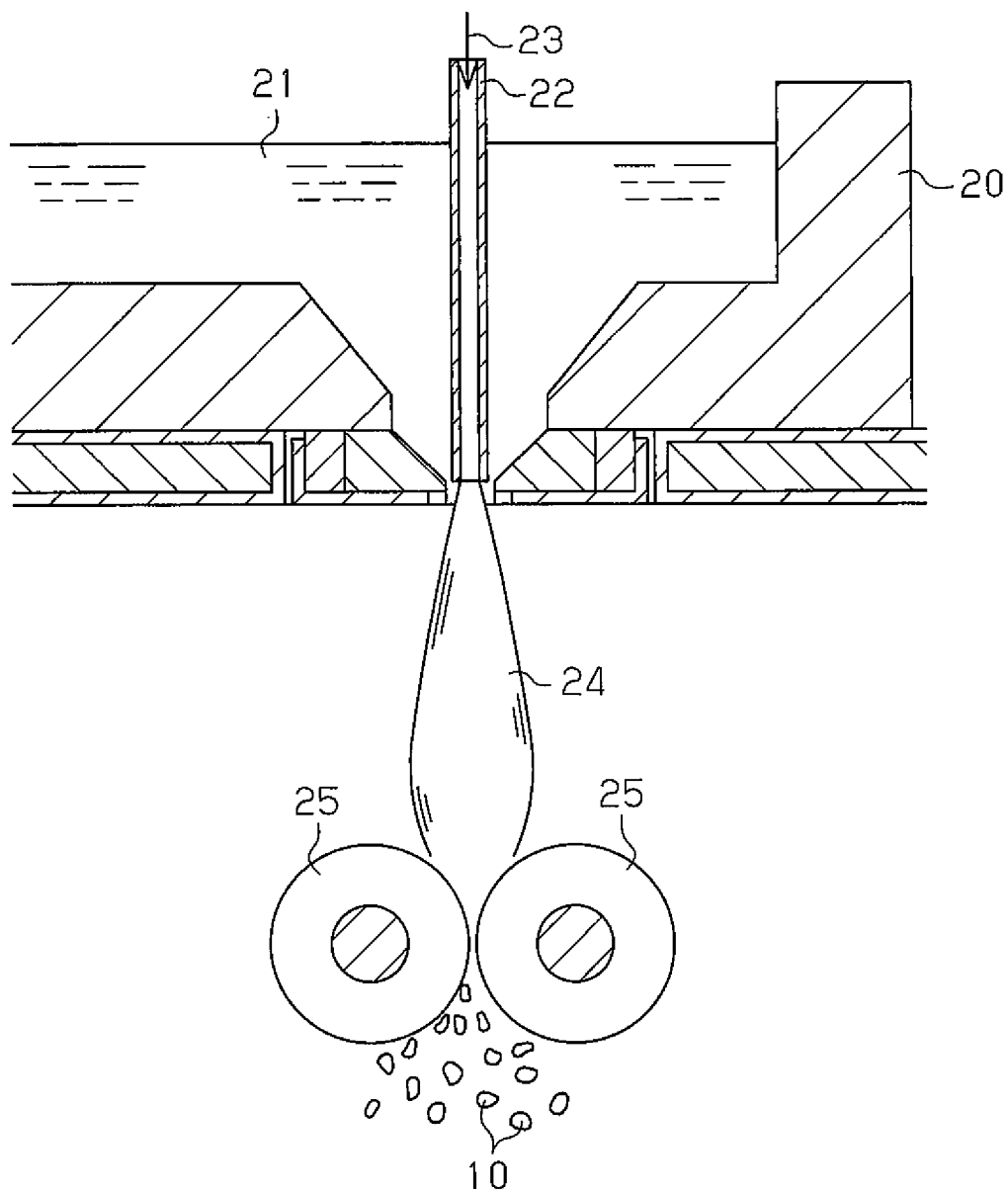
FIG. 4 is a cross-sectional view showing an apparatus for fabricating the glass flakes.

The glass flake 10 of the present embodiment may be fabricated using, for example, a fabrication apparatus that is shown in FIG. 4. Referring to FIG. 4, a glass base material 21, which is melted in a fire-retardant kiln basin and has the glass composition described above, is inflated by gas 23 delivered through a blow nozzle 22 into a balloon to form a hollow glass film 24. The resulting hollow glass film 24 is crushed by two pressing rollers 25 to obtain glass flakes 10.

The glass flake 10 of the present embodiment may also be fabricated using, for example, a fabrication apparatus that is shown in FIG. 5. Referring to FIG. 5, a molten-state glass base material 21, which is poured into a rotary cup 26 and has the glass composition described above, is centrifugally discharged in radial direction from the upper end of the rotary cup 26, is aspirated by air flow via a gap between upper and lower annular plates 27, and is introduced into an annular cyclone-type collector 28. When passing through the gap between the annular plates 27, the glass base material 21 is cooled, becomes solidified into a thin film shape, and is crushed to fine pieces to obtain glass flakes 10.

Physical Properties of Glass Composition

The physical properties of the glass flakes 10 in the present embodiment will now be discussed in detail.

(Thermal Property)

The temperature when the viscosity of molten glass is 100 Pa·sec (1000 P) is referred to as the working temperature and is most suitable for glass forming the glass flakes 10. For example, with the fabrication apparatus of FIG. 4, the average thickness of the hollow glass film 24, that is, the average thickness of the glass flakes 10, is 0.1 to 15 μm. When forming such a thin hollow glass film 24, the temperature of the glass decreases drastically. Due to the temperature decrease, the plasticity of the hollow glass film 24 suddenly decreases and makes the hollow glass film 24 difficult to elongate. The decrease in plasticity makes it difficult for the hollow glass film 24 to grow uniformly, and variations may occur in the glass film thickness. Thus, the working temperature is preferably 1100° C. or greater, more preferably 1150° C. or greater, even more preferably 1180° C. or greater, and most preferably 1200° C. or greater.

When the working temperature exceeds 1300° C., the glass fabrication apparatus is apt to being corroded by heat. This may shorten the life of the apparatus. Further, a lower working temperature would reduce the cost of fuel required to melt glass crude material. Thus, the working temperature is preferably 1300° C. or less, more preferably 1280° C. or less, even more preferably 1260° C. or less, and most preferably 1250° C. or less. The devitrification temperature is about 1100° C. to 1250° C. In this specification, devitrification refers to a situation in which crystals generated and grown from the glass base material 21 become turbid. Glass fabricated from such molten glass base material 21 may include crystallized agglomerates and thus is not preferable for use as a glass flake 10.

An increase in the temperature difference ΔT, which is obtained by subtracting the devitrification temperature from the working temperature, would result in devitrification being less likely to occur during glass forming, and homogeneous glass flakes 10 may be fabricated with a high yield. For example, the fabrication apparatus shown in FIGS. 4 and 5 may be used to fabricate the glass flakes 10 with a high yield when glass having a temperature difference ΔT of 0° C. or greater is used. Accordingly, ΔT is preferably 0° C. or greater, more preferably 20° C. or greater, even more preferably 40° C. or greater, and most preferably 50° C. or greater. However, to facilitate adjustments in the glass composition, it is preferable that ΔT be 200° C. or less. It is more preferable that ΔT be 180° C. or less and particularly preferable that ΔT be 150° C. or less.

(Glass Transition Temperature)

The glass flakes 10 have a heat resistance that increases as the glass transition temperature (glass transition point, Tg) increases and become difficult to deform when undergoing processing that requires heating to a high temperature. As long as the glass transition temperature is 560° C. or greater, the shapes of the glass flakes 10 are unlikely to change in a process for forming on the surfaces of the glass flakes 10 a coating of which main component is a metal or metal oxide. The glass flakes 10 or coated glass flakes may be blended with paint and be used for an application such as baking finishing. The glass composition specified in the present embodiment easily obtains glass having a glass transition temperature of 560° C. or greater. The glass transition temperature of the glass flakes 10 is preferably 560° C. or greater, more preferably 580° C. or greater, and even more preferably 600° C. or greater. The upper limit of the glass transition temperature is preferably about 750° C.

(Chemical Durability)

The glass flakes 10 of the present embodiment having superior chemical durability, such as acid resistance, water resistance, and alkali resistance. Thus, the glass flakes 10 of the present embodiment are optimal for use in applications such as a resin mold product, paint, cosmetics, and ink.

As an index for acid resistance, a mass decrease rate ΔW measured as follows was used. The glass base material for fabricating the glass flakes 10 was crushed and passed through a supplemental mesh sieve of 710 μm and a standard mesh sieve of 590 μm, which are specified by JIS Z 8801. An amount of glass powder with a size that did not pass through a standard mesh sieve of 420 μm corresponding to the same grams as the specific gravity of glass was immersed for 72 hours in 100 mL of 10 percent by mass of a sulfuric acid aqueous solution at 80° C. to obtain the mass decrease rate ΔW. A lower mass decrease rate ΔW indicates higher acid resistance. This measurement method is in compliance with "Measurement Method (Powder Method) of Chemical Durability for Optical Glass" of the Japan Optical Glass Industrial Standard (JOGIS). However, in the examples described later, instead of using 0.01 N (mol/L) of nitric acid aqueous solution as specified by the JOGIS measurement method, 10 percent by mass of sulfuric acid aqueous solution was used. The temperature of the sulfuric acid aqueous solution was set to 80° C., and the liquid amount was set to 100 mL instead of the 80 mL in the JOGIS measurement method. Further, the processing time was 72 hours instead of the 60 minutes in the JOGIS measurement method. The glass base material for fabricating the glass flakes 10 is a glass sample manufactured by melting conventional glass crude materials.

When using paint or the like containing the glass flakes 10 as corrosion-resistant lining under an acid environment, it is desirable that the above-described index (mass decrease rate ΔW) indicating the acid resistance of glass be a small value. When the mass decrease rate ΔW is a large value, the corrosion resistance of the corrosion-resistant lining under an acid environment becomes low. Accordingly, the mass decrease rate ΔW is preferably 1.2 percent by mass or less, more preferably 0.8 percent by mass or less, even more preferably 0.5 percent by mass or less, and most preferably 0.4 percent by mass or less. The lower limit for the mass decrease rate ΔW is normally about 0.05 percent by mass.

Coated Glass Flake

Figure 2:
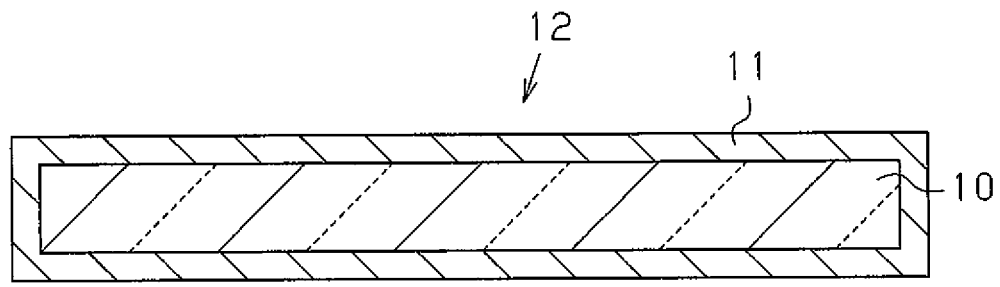
FIG. 2 is a schematic cross-sectional view showing a coated glass flake.

As schematically shown in FIG. 2, a coating 11 of which a main component is metal or a metal oxide is formed on the surface of the above-described glass flake 10 as a core to fabricate a coated glass flake 12. It is preferable that the coating 11 be formed by at least one of a metal and a metal oxide. The coating 11 may have any one of a single layer, mixed layer, and multiple layer structure.

More specifically, the coating 11 is formed from at least one metal selected from the group consisting of silver, gold, platinum, palladium, and nickel. Alternatively, the coating 11 is formed from at least one metal oxide selected from the group consisting of titanium oxides, aluminum oxide, iron oxides, cobalt oxides, zirconium oxide, zinc oxide, tin oxides, and silicon dioxide. Among these substances, titanium dioxide, which has a high refractive index and transparency and in which coloring of an interference color is satisfactory, and iron oxide, which can produce a characteristic color, are preferable.

The coating 11 may be a laminated film including a first film, of which a main component is a metal, and a second film, of which a main component is a metal oxide.

The coating 11 may be formed on the entire surface of the glass flake 10, which serves as the core. Alternatively, the coating 11 may be formed on part of the surface of the glass flake 10.

The coating 11 may have a thickness that is set in accordance with the application. Any process such as a generally known process may be employed as a process for forming the coating 11 on the glass flake 10. For example, a known process may be employed such as a sputtering process, a sol-gel process, a chemical vapor deposition (CVD), or an LPD process (a liquid phase deposition process for depositing an oxide from a metal salt process) may be employed. The LPD process (liquid phase deposition process) is a method for depositing a metal oxide on a substrate or like from a reaction solution.

Application (Resin Composition, Paint, Ink Composition, and Cosmetics)

Figure 3:
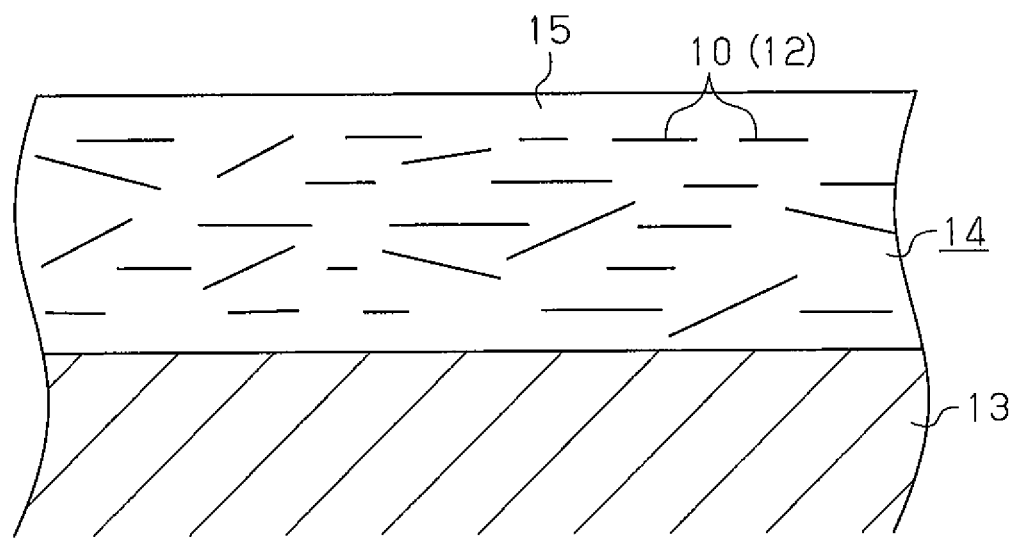
FIG. 3 is a cross-sectional view showing a state in which a coating film including glass flakes or coated glass flakes is formed on the surface of a substrate.

The glass flakes 10 or coated glass flakes 12 are blended as a pigment or reinforcement filler by a known means with a resin composition, paint, ink composition, cosmetics, and the like. This increases the color tone and lust of the resin composition, paint, ink composition, cosmetics, and the like. Further, the dimensional accuracy, strength, and the like are improved when using such resin composition, paint, and ink composition. FIG. 3 is a schematic cross-sectional view of a sample of a substrate 13 having a surface on which a coating film prepared by blending the glass flakes 10 with paint is applied. As shown in FIG. 3, the glass flakes 10 or coated glass flakes 12 are dispersed in a resin matrix 15 of a coating film 14.

The resin composition, paint, ink composition, and cosmetics may be selected and used as required in accordance with the application as long as it is generally known. The mixture ratio of the glass flakes 10 and these materials may be set as required. Further, the method for blending the glass flakes 10 with these materials may be any method that is generally known. For example, when blending the glass flakes 10 or the coated glass flakes 12 with paint, a thermosetting resin, a thermoplastic resin, or a curing agent may be selected as required and be mixed with the host material resin.

The thermosetting resin is not particularly limited and may be acrylic resin, polyester resin, epoxy resin, phenol resin, urea resin, fluorocarbon resin, polyester-urethane curable resin, epoxy-polyester curable resin, acryl-polyester resin, acryl-urethane curable resin, acryl-melamine curable resin, polyester-melamine curable resin, and the like.

The thermoplastic resin is not particularly limited and may be, for example, polyvinyl chloride, polypropylene, polyethylene, polystyrene, polyester, polyamide, polycarbonate, polybutylene, polybutylene terephthalate, or a copolymer of monomers forming these substances, poly phenylene sulfide, polyphenylene ether, polyetheretherketone, liquid crystal polymer (type I, type II, or type III), thermoplastic fluorocarbon resin, and the like.

The curing agent is not particularly limited and may be polyisocyanate, amine, polyamide, polybasic acid, acid anhydride, polysulfide, boron trifluoride acid, acid dihydrazide, imidazole, and the like.

Further, when blending the glass flakes 10 or the coated glass flakes 12 with a resin composition, any of the above-described thermosetting resins or thermoplastic resins may be used as the host resin.

The ink composition may be an ink for a writing implement such as any type of ballpoint and felt tip pens or printing ink such as gravure and offset inks. The glass flakes 10 or the coated glass flakes 12 may be applied to any of such ink compositions. The vehicle forming the ink composition scatters the pigment and functions to solidify the ink on paper. The vehicle is formed from a resin, oil, and solvent.

Examples of the resin for the vehicle of a writing implement ink include an acrylic resin, a styrene-acrylic copolymer, polyvinyl alcohol, polyacrylate, acrylic monomer-vinyl acetate copolymer, a microbial polysaccharide such as xanthan gum, and a water-soluble polysaccharide such as guar gum. Further, examples of the solvent include water, alcohol, hydrocarbon, ester, and the like.

Examples of the gravure ink vehicle include resins, such as gum rosin, wood rosin, tall oil rosin, lime rosin, rosin ester, a maleic resin, a polyamide resin, a vinyl resin, cellulose nitrate, cellulose acetate, ethyl cellulose, chlorinated rubber, cyclized rubber, an ethylene-vinyl acetate copolymer resin, an urethane resin, a polyester resin, an alkyd resin, gilsonite, dammar, shellac, or the like, a mixture of these resins, and a water-soluble resin or emulsion resin in which the above-described resins are dissolved. Examples of the solvent include hydrocarbon, alcohol, ether, ester, and water.

Examples of the offset ink vehicle include resins, such as a rosin-modified phenol resin, a petroleum resin, an alkyd resin, and a dry modified resin obtained from any one of these resins, and oils, such as linseed oil, tung oil, and soybean oil. Examples of the solvent include n-paraffin, isoparaffin, aromatic, naphthene, alpha-olefin, and water. Conventional additives, such as a dye, pigment, surfactant, lubricant, defoamer, and leveling agent may be selected and mixed to each of the vehicle components described above.

Examples of the cosmetics include a wide variety of cosmetics such as facial cosmetics, makeup cosmetics, and hair cosmetics. Among these cosmetics, application is optimal for makeup cosmetics, such as foundation, face powder, eye shadow, makeup base, nail enamel, eye liner, mascara, lipstick, and fancy powder.

In accordance with the application to cosmetics, a hydrophobizing process may be performed on the glass flakes 10 when required. The hydrophobizing process may be performed through any of the five processes described below.

(1) Process using a silicone compound such as methyl hydrogen polysiloxane, high-viscosity silicone oil or a silicone resin.

(2) Process using a surfactant such as an anion surfactant or a cationic surfactant.

(3) Process using a polymer compound such as nylon, polymethylmethacrylate, polyethylene, various types of fluorocarbon resin [polytetrafluoroethylene resin (PTFE), tetrafluoroethylene-perfluoro alkyl vinyl ether copolymer (PFA), tetrafluoroethylene-hexafluoropropylene copolymer (FEP), Tetrafluoroethylene-ethylene copolymer (ETFE), polyvinylidene fluoride (PVDF), polychlorotrifluoroethylene (PCTFE), and the like], polyamino acid.

(4) Process using a perfluoro group-containing compound, lecithin, collagen, metal soap, lipophilic wax, polyalcohol partial ester or complete ester and the like.

(5) Process combining the above processes.

Processes other than those described above may be used as long as it includes hydrophobize powder.

Other materials that are commonly used for cosmetics may be blended with the above-mentioned cosmetics when required. For example, inorganic powder, organic powder, pigment or colorant, an ester, an oil component, an organic solvent, a resin, a plasticizer, an ultraviolet absorbent, an antioxidant, a preservative, a surfactant, a moisturizer, a perfume, water, alcohol, and a thickening agent may be used.

Examples of an inorganic powder include talc, kaolin, sericite, white mica, black mica, lithia mica, vermiculite, magnesium carbonate, calcium carbonate, diatomaceous earth, magnesium silicate, calcium silicate, aluminium silicate, barium sulfate, metal salts of tungstic acid, silica, hydroxyapatite, zeolite, boron nitride, and ceramic powder.

Examples of an organic powder include nylon powder, polyethylene powder, polystyrene powder, benzoguanamine powder, polytetrafluoroethylene powder, (distyrenebenzene polymer powder), epoxy resin powder, acrylic resin powder, and microcrystalline cellulose.

The pigment is largely classified into inorganic pigments and organic pigments.

Examples of inorganic pigments include the following as categorized in accordance with color. Inorganic white pigment: titanium oxide and zinc oxide. Inorganic red pigment: iron oxide (colcothar) and iron titanate. Inorganic brown pigments: γ-iron oxide. Inorganic yellow pigments: yellow iron oxide and yellow earth. Inorganic black pigments: black iron oxide and carbon black. Inorganic violet pigments: mango violet and cobalt violet. Inorganic green pigments: cobalt titanate. Inorganic blue pigments: such as ultramarine and Prussian blue.

Examples of pearl pigments include titanium oxide coated mica, titanium oxide coated bismuth oxychloride, bismuth oxychloride, titanium oxide coated talc, fish scale foil, and colored titanium oxide coated mica. Further, metal powder pigments include aluminum powder and copper powder.

Examples of organic pigments include red No. 201, red No. 202, red No. 204, red No. 205, red No. 220, red No. 226, red No. 228, red No. 405, orange No. 203, orange No. 204, yellow No. 205, yellow No. 401, and blue No. 404.

For an extender pigment such as talc, calcium carbonate, barium sulfate, zirconium oxide, and aluminum white, the organic pigments obtained by laking the dyes described below were used. Examples of dyes includes red No. 3, red No. 104, red No. 106, red No. 227, red No. 230, red No. 401, red No. 505, orange No. 205, yellow No. 4, yellow No. 5, yellow No. 202, yellow No. 203, green No. 3, blue No. 1, and the like. Further, examples of colorants include natural colorants such as chlorophyll and β-carotene.

Examples of hydrocarbons include squalane, fluid paraffin, fluid polyisobutylene, vaseline, micro-crystalline wax, ozokerite, ceresin, myristic acid, palmitic acid, stearic acid, oleic acid, isostearic acid, cetyl alcohol, hexyldecanol, oleyl alcohol, hexadecyl 2-ethylhexanoate, palmitic acid 2-ethylhexyl ester, 2-octyldodecyl myristate, neopentyl glycol di-2-ethylhexanoate, glycerol tris(2-ethylhexanoate), 2-octyldodecyl oleate, isopropyl myristate, glycerol triisostearate, glycerol tri(coconut oil fatty acid) ester, olive oil, avocado oil, beeswax, myristyl myristate, mink oil, and lanolin.

Further examples of the esters include silicone oil, higher fatty acids, oils and fats and the like. Examples of the oil components include higher alcohols wax and the like. Examples of organic solvents include acetone, toluene, butyl acetate, and ester acetate. Examples of resins include alkyd resin and urea resin and the like. Examples of plasticizers include camphor, acetyltributyl citrate and the like. In addition, ultraviolet absorbents, antioxidants, preservatives, surfactants, moisturizers, perfume, water, alcohol, thickening agents and the like may be used.

The form of the cosmetics is not particularly limited and may be in the form of powder, cake, pencils, sticks, paste, liquid, emulsion, cream, and the like.

The advantages of the above-discussed embodiment will now be described.

In the glass flakes 10 of the present embodiment, the composition of the glass base material for fabricating the glass flakes 10 is set to be $60 \leq SiO_2 \leq 70$ and $5 \leq Al_2O_3 \leq 15$. This obtains the sufficient content of silicon dioxide and aluminum oxide, and the silicon dioxide and aluminum oxide function to sufficiently form the skeleton for glass. Further, the glass transition temperature is high, the meltability is satisfactory, and the acid resistance and water resistance are increased. Further, the content of lithium oxide, sodium oxide, and potassium oxide is set to be $4 < (Li_2O + Na_2O + K_2O) < 9$. This adjusts the devitrification temperature and viscosity in a satisfactory manner. In addition, the contents of magnesium oxide and calcium oxide are set to be $1 \leq MgO \leq 10$ and $10 \leq CaO \leq 25$. This adjusts the devitrification temperature and viscosity in a satisfactory manner, while maintaining the heat resistance of glass.

Accordingly, the heat resistance and chemical durability of the glass flakes 10 are increased. The superior heat resistance suppresses deformation when the glass flakes 10 are heated to a high temperature. Further, due to the superior acid resistance, the glass flakes 10 may be applied to, for example, a corrosion-resistant lining under an acidic environment and is effective when used as a base material for a coating formed through liquid phase processing using an acid solution. Further, the working temperature may be controlled at a relatively low temperature. This facilitates the fabrication of the glass flakes 10.

The temperature difference ΔT obtained by subtracting the devitrification temperature from the working temperature for the glass base material for fabricating the glass flakes 10 is set to be 0° C. to 200° C. This suppresses devitrification when forming glass and obtains further homogeneous glass flakes 10.

The transition temperature of the glass base material for fabricating the glass flakes 10 is to be from 560° C. to 750° C. This increases the acid resistance of the glass flakes 10.

Index ΔW, which indicates the acid resistance of the glass base material for fabricating the glass flakes 10 is set at 0.05 to 1.2 percent by mass. This increases the acid resistance of the glass flakes.

In the coated glass flake 12, the surface of a glass flake 10 is coated with the coating 11, the main component of which is metal or metal oxide. The coating 11 allows for coloring to a metallic color or interference color. Accordingly, the coated glass flakes 12 are optimal for use as a luster pigment.

The above-discussed embodiment will now be further specifically described. However, the present invention is not limited to the examples.

EXAMPLES 1 TO 60 AND COMPARATIVE EXAMPLES 1 TO 11

The compositions shown in tables 1 to 7 were prepared by mixing conventional glass crude materials, such as silica sand and the like to produce batches of glass base material for each example and comparative example. An electrical furnace was used to heat each batch to 1400° C. to 1600° C. and melt the batch. This condition was then maintained for about four hours until the composition became uniform. Then, the molten glass base material was poured into a steel plate and slowly cooled to room temperature in the electrical furnace to obtain a glass sample.

The coefficient of thermal expansion for the glass sample prepared in this manner was measured with a commercially available dilatometer (Rigaku Corporation, Thermomechanical Analyzer TMA 8510), and the glass transition temperature was obtained from a coefficient of thermal expansion curve. The relationship between the viscosity and temperature was checked using the conventional platinum ball lifting process, and the working temperature was obtained from the results. In the platinum lifting process, first a platinum ball is immersed in molten glass. Then, to measure the viscosity the relationship of the load (resistance) when lifting the platinum ball at a constant velocity and the gravity or buoyant force that acts on the platinum ball are applied using Stokes's theorem, which indicates the relationship between viscosity and falling velocity when a microscopic grain settles in a fluid.

The glass sample was crushed, and the fragments of a size that passes through a standard mesh sieve of 1.0 mm, as specified by JIS Z 8801, but does not pass through a standard mesh sieve of 2.8 mm were put into a platinum boat and heated with a temperature gradient (900° C. to 1400° C.) for two hours in an electrical furnace. Then, the devitrification temperature was obtained from the maximum temperature of the electrical furnace in correspondence to the positions at which crystals appeared. To compensate for variations in the temperature behavior depending on location in the electrical furnace, the temperature behavior at a predetermined location in the electrical furnace was measured beforehand. The glass sample was arranged in the predetermined location to measure the devitrification temperature.

Tables 1 to 7 show the measurement results. The glass compositions shown in tables 1 to 7 are all values expressed in percent by mass. Here, ΔT is the temperature difference obtained by subtracting the devitrification temperature from the working temperature as described above, and ΔW is the index for acid resistance as described above. The glass sample was crushed. An amount of glass powder with a size that passed through a supplemental mesh sieve of 710 μm and a standard mesh sieve of 590 μm, which are specified by JIS Z 8801, but did not pass through a standard mesh sieve of 420 μm corresponding to the same grams as the specific gravity of glass was collected and immersed for 72 hours in 100 mL of 10 percent by mass of a sulfuric acid aqueous solution at 80° C. to obtain the mass decrease rate.

TABLE 1

| Component (mass %) or Physical Property | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| $SiO_2$ | 66.17 | 66.53 | 66.39 | 65.91 | 66.59 | 66.14 | 66.16 | 64.48 | 64.82 | 64.11 |
| $B_2O_3$ | — | — | — | — | — | — | — | — | — | — |
| $Al_2O_3$ | 11.13 | 11.19 | 11.17 | 11.09 | 11.20 | 11.13 | 11.13 | 11.01 | 11.07 | 11.87 |
| MgO | 2.08 | 2.09 | 2.09 | 2.07 | 2.09 | 2.07 | 2.08 | 2.86 | 2.87 | 2.86 |
| CaO | 15.94 | 16.02 | 15.99 | 15.41 | 16.04 | 15.86 | 15.93 | 14.66 | 14.73 | 14.68 |
| SrO | — | — | — | 0.86 | — | — | — | — | — | — |
| BaO | — | — | — | — | — | — | — | — | — | — |
| ZnO | — | — | — | — | — | — | — | — | — | — |
| $Li_2O$ | 2.31 | 2.82 | 2.47 | 2.30 | 3.07 | 2.31 | 2.31 | 1.30 | 1.80 | 1.80 |
| $Na_2O$ | 1.88 | 0.86 | 1.89 | 1.87 | — | 1.88 | 1.88 | 3.90 | 2.89 | 2.88 |
| $K_2O$ | 0.48 | 0.49 | — | 0.48 | 1.01 | 0.48 | 0.48 | 0.48 | 0.48 | 0.48 |
| $Li_2O + Na_2O + K_2O$ | 4.67 | 4.17 | 4.36 | 4.65 | 4.08 | 4.67 | 4.67 | 5.68 | 5.17 | 5.16 |
| $TiO_2$ | — | — | — | — | — | 0.13 | — | 1.31 | 1.32 | 1.31 |
| $ZrO_2$ | — | — | — | — | — | — | — | — | — | — |
| $Fe_2O_3$ | — | — | — | — | — | — | 0.03 | — | — | — |
| Glass Transition Temperature [° C.] | 610 | 607 | 609 | 610 | 605 | 613 | 612 | 627 | 615 | 613 |
| Devitrification Temperature [° C.] | 1179 | 1151 | 1176 | 1175 | 1157 | 1178 | 1179 | 1185 | 1174 | 1174 |
| Working Temperature [° C.] | 1239 | 1238 | 1238 | 1240 | 1226 | 1241 | 1240 | 1246 | 1240 | 1237 |
| ΔT [° C.] | 60 | 87 | 62 | 65 | 69 | 63 | 61 | 61 | 66 | 63 |
| ΔW [mass %] | 0.12 | 0.09 | 0.12 | 0.12 | 0.08 | 0.12 | 0.12 | 0.21 | 0.25 | 0.30 |

TABLE 2

| Component (mass %) or Physical Property | Ex. 11 | Ex. 12 | Ex. 13 | Ex. 14 | Ex. 15 | Ex. 16 | Ex. 17 | Ex. 18 | Ex. 19 | Ex. 20 |
|---|---|---|---|---|---|---|---|---|---|---|
| $SiO_2$ | 64.69 | 63.98 | 64.43 | 63.77 | 64.22 | 64.72 | 64.63 | 64.47 | 66.47 | 67.30 |
| $B_2O_3$ | — | — | — | — | — | — | — | — | — | — |
| $Al_2O_3$ | 11.05 | 11.85 | 11.84 | 11.81 | 11.80 | 11.89 | 11.04 | 11.01 | 9.41 | 9.53 |
| MgO | 2.87 | 2.86 | 2.79 | 2.85 | 2.78 | 2.94 | 2.94 | 2.86 | 2.19 | 2.22 |
| CaO | 14.70 | 14.65 | 14.28 | 14.61 | 14.23 | 15.07 | 15.05 | 14.64 | 16.20 | 16.40 |
| SrO | — | — | — | — | — | — | — | — | — | — |
| BaO | — | — | — | — | — | — | — | — | — | — |
| ZnO | — | — | — | — | — | — | — | — | — | — |
| $Li_2O$ | 1.46 | 1.46 | 1.46 | 1.30 | 1.30 | 1.46 | 1.31 | 1.30 | 1.31 | 2.33 |
| $Na_2O$ | 3.91 | 3.90 | 3.89 | 3.88 | 3.88 | 3.91 | 3.91 | 3.90 | 3.93 | 2.22 |
| $K_2O$ | — | — | — | 0.48 | 0.48 | — | 0.48 | 0.48 | 0.48 | — |
| $Li_2O + Na_2O + K_2O$ | 5.37 | 5.36 | 5.35 | 5.66 | 5.66 | 5.37 | 5.70 | 5.68 | 5.72 | 4.55 |
| $TiO_2$ | 1.32 | 1.31 | 1.31 | 1.31 | 1.31 | — | 0.66 | 1.31 | — | — |
| $ZrO_2$ | — | — | — | — | — | — | — | — | — | — |
| $Fe_2O_3$ | — | — | — | — | — | — | — | 0.03 | — | — |
| Glass Transition Temperature [° C.] | 625 | 628 | 623 | 632 | 628 | 623 | 628 | 622 | 626 | 607 |
| Devitrification Temperature [° C.] | 1185 | 1183 | 1183 | 1186 | 1183 | 1191 | 1186 | 1180 | 1200 | 1187 |
| Working Temperature [° C.] | 1241 | 1242 | 1251 | 1246 | 1255 | 1249 | 1244 | 1245 | 1249 | 1232 |
| ΔT [° C.] | 56 | 59 | 68 | 60 | 72 | 58 | 58 | 65 | 49 | 45 |
| ΔW [mass %] | 0.30 | 0.35 | 0.32 | 0.36 | 0.33 | 0.27 | 0.27 | 0.29 | 0.13 | 0.08 |

TABLE 3

| Component (mass %) or Physical Property | Ex. 21 | Ex. 22 | Ex. 23 | Ex. 24 | Ex. 25 | Ex. 26 | Ex. 27 | Ex. 28 | Ex. 29 | Ex. 30 |
|---|---|---|---|---|---|---|---|---|---|---|
| $SiO_2$ | 63.68 | 64.31 | 64.08 | 64.36 | 65.13 | 66.96 | 66.27 | 66.33 | 64.49 | 65.40 |
| $B_2O_3$ | — | — | — | — | — | — | — | — | — | — |
| $Al_2O_3$ | 10.96 | 11.07 | 11.03 | 11.08 | 14.29 | 11.18 | 11.06 | 11.07 | 11.10 | 11.09 |
| MgO | 2.86 | 3.09 | 2.79 | 2.95 | 1.84 | 4.66 | 1.95 | 2.38 | 2.83 | 2.82 |
| CaO | 17.77 | 15.82 | 14.32 | 15.09 | 14.14 | 11.96 | 15.54 | 14.04 | 15.12 | 12.53 |
| SrO | — | — | — | — | — | — | — | — | — | — |
| BaO | — | — | — | — | — | — | — | — | — | — |
| ZnO | — | — | — | — | — | — | — | — | — | — |
| $Li_2O$ | 0.22 | 1.31 | 1.80 | 1.81 | 2.27 | 1.82 | 1.80 | 1.85 | 1.85 | 1.95 |
| $Na_2O$ | 4.17 | 3.92 | 2.88 | 2.90 | 1.85 | 2.92 | 2.89 | 3.78 | 3.78 | 5.53 |
| $K_2O$ | 0.34 | 0.48 | 0.48 | 0.48 | 0.48 | 0.49 | 0.48 | 0.54 | 0.55 | 0.68 |
| $Li_2O + Na_2O + K_2O$ | 4.73 | 5.71 | 5.16 | 5.19 | 4.60 | 5.23 | 5.17 | 6.17 | 6.18 | 8.16 |
| $TiO_2$ | — | — | 2.63 | 1.32 | — | — | — | — | 0.26 | — |
| $ZrO_2$ | — | — | — | — | — | — | — | — | — | — |
| $Fe_2O_3$ | — | — | — | 0.03 | — | — | — | — | — | — |
| Glass Transition Temperature [° C.] | 683 | 627 | 616 | 625 | 631 | 618 | 613 | 603 | 607 | 584 |
| Devitrification Temperature [° C.] | 1228 | 1198 | 1175 | 1181 | 1136 | 1230 | 1200 | 1180 | 1177 | 1170 |
| Working Temperature [° C.] | 1271 | 1242 | 1232 | 1226 | 1278 | 1283 | 1257 | 1253 | 1221 | 1228 |
| ΔT [° C.] | 43 | 44 | 57 | 45 | 142 | 53 | 57 | 73 | 44 | 58 |
| ΔW [mass %] | 0.39 | 0.28 | 0.34 | 0.27 | 0.21 | 0.18 | 0.14 | 0.14 | 0.18 | 0.17 |

TABLE 4

| Component (mass %) or Physical Property | Ex. 31 | Ex. 32 | Ex. 33 | Ex. 34 | Ex. 35 | Ex. 36 | Ex. 37 | Ex. 38 | Ex. 39 | Ex. 40 |
|---|---|---|---|---|---|---|---|---|---|---|
| $SiO_2$ | 65.36 | 64.21 | 65.38 | 64.58 | 65.10 | 66.40 | 65.16 | 65.34 | 63.60 | 64.48 |
| $B_2O_3$ | — | — | — | — | — | — | — | — | — | — |
| $Al_2O_3$ | 11.08 | 11.05 | 11.08 | 10.95 | 11.03 | 11.09 | 11.04 | 11.07 | 10.95 | 11.10 |
| MgO | 2.29 | 2.85 | 2.19 | 3.25 | 2.61 | 2.82 | 3.04 | 2.38 | 3.24 | 3.01 |
| CaO | 15.10 | 15.21 | 16.16 | 13.55 | 14.58 | 12.53 | 13.08 | 14.04 | 13.56 | 15.43 |
| SrO | — | — | — | — | — | — | — | — | — | — |
| BaO | — | — | — | — | — | — | — | — | — | — |
| ZnO | — | — | — | — | — | — | — | — | — | — |
| $Li_2O$ | 1.85 | 1.35 | 1.81 | 0.37 | 1.35 | 1.90 | 1.40 | 1.90 | 0.41 | 1.81 |
| $Na_2O$ | 3.78 | 4.79 | 2.90 | 6.77 | 4.78 | 4.65 | 5.65 | 4.64 | 7.62 | 2.90 |
| $K_2O$ | 0.54 | 0.54 | 0.48 | 0.54 | 0.54 | 0.62 | 0.62 | 0.62 | 0.61 | 0.48 |

TABLE 4-continued

| Component (mass %) or Physical Property | Ex. 31 | Ex. 32 | Ex. 33 | Ex. 34 | Ex. 35 | Ex. 36 | Ex. 37 | Ex. 38 | Ex. 39 | Ex. 40 |
|---|---|---|---|---|---|---|---|---|---|---|
| $Li_2O + Na_2O + K_2O$ | 6.17 | 6.68 | 5.19 | 7.68 | 6.67 | 7.17 | 7.67 | 7.16 | 8.64 | 5.19 |
| $TiO_2$ | — | — | — | — | — | — | — | — | — | 0.79 |
| $ZrO_2$ | — | — | — | — | — | — | — | — | — | — |
| $Fe_2O_3$ | — | — | — | — | — | — | — | — | — | — |
| Glass Transition Temperature [° C.] | 609 | 610 | 620 | 646 | 618 | 590 | 597 | 595 | 625 | 623 |
| Devitrification Temperature [° C.] | 1188 | 1193 | 1193 | 1210 | 1198 | 1173 | 1185 | 1178 | 1201 | 1187 |
| Working Temperature [° C.] | 1234 | 1237 | 1237 | 1277 | 1247 | 1260 | 1249 | 1232 | 1255 | 1228 |
| ΔT [° C.] | 46 | 44 | 44 | 67 | 49 | 87 | 64 | 54 | 54 | 41 |
| ΔW [mass %] | 0.15 | 0.28 | 0.17 | 0.29 | 0.22 | 0.14 | 0.21 | 0.18 | 0.34 | 0.18 |

TABLE 5

| Component (mass %) or Physical Property | Ex. 41 | Ex. 42 | Ex. 43 | Ex. 44 | Ex. 45 | Ex. 46 | Ex. 47 | Ex. 48 | Ex. 49 | Ex. 50 |
|---|---|---|---|---|---|---|---|---|---|---|
| $SiO_2$ | 65.94 | 65.06 | 64.51 | 64.53 | 63.29 | 63.67 | 65.48 | 64.83 | 64.28 | 64.87 |
| $B_2O_3$ | — | — | — | — | — | — | — | 0.57 | 1.15 | — |
| $Al_2O_3$ | 11.01 | 11.03 | 11.10 | 11.11 | 10.89 | 12.62 | 11.10 | 11.07 | 11.06 | 11.00 |
| MgO | 2.57 | 2.80 | 3.05 | 2.96 | 2.81 | 2.59 | 2.42 | 2.19 | 2.19 | 2.17 |
| CaO | 11.84 | 12.46 | 13.15 | 14.22 | 14.99 | 14.48 | 16.80 | 16.15 | 16.14 | 15.12 |
| SrO | — | — | — | — | — | — | — | — | — | 1.70 |
| BaO | — | — | — | — | — | — | — | — | — | — |
| ZnO | — | — | — | — | — | — | — | — | — | — |
| $Li_2O$ | 1.45 | 1.45 | 1.95 | 1.90 | — | 1.34 | 1.76 | 1.80 | 1.80 | 1.79 |
| $Na_2O$ | 6.51 | 6.52 | 5.54 | 4.66 | 7.49 | 4.75 | 2.03 | 2.89 | 2.89 | 2.87 |
| $K_2O$ | 0.68 | 0.68 | 0.69 | 0.62 | 0.54 | 0.54 | 0.41 | 0.48 | 0.48 | 0.48 |
| $Li_2O + Na_2O + K_2O$ | 8.64 | 8.65 | 8.18 | 7.18 | 8.03 | 6.63 | 4.20 | 5.17 | 5.17 | 5.14 |
| $TiO_2$ | — | — | — | — | — | — | — | — | — | — |
| $ZrO_2$ | — | — | — | — | — | — | — | — | — | — |
| $Fe_2O_3$ | — | — | — | — | — | — | — | — | — | — |
| Glass Transition Temperature [° C.] | 590 | 591 | 586 | 598 | 652 | 623 | 632 | 617 | 616 | 616 |
| Devitrification Temperature [° C.] | 1177 | 1177 | 1173 | 1173 | 1227 | 1184 | 1180 | 1182 | 1172 | 1182 |
| Working Temperature [° C.] | 1264 | 1244 | 1214 | 1222 | 1268 | 1248 | 1245 | 1225 | 1215 | 1239 |
| ΔT [° C.] | 87 | 67 | 41 | 49 | 41 | 64 | 65 | 43 | 43 | 57 |
| ΔW [mass %] | 0.15 | 0.20 | 0.28 | 0.23 | 0.40 | 0.33 | 0.17 | 0.21 | 0.26 | 0.17 |

TABLE 6

| Component (mass %) or Physical Property | Ex. 51 | Ex. 52 | Ex. 53 | Ex. 54 | Ex. 55 | Ex. 56 | Ex. 57 | Ex. 58 | Ex. 59 | Ex. 60 |
|---|---|---|---|---|---|---|---|---|---|---|
| $SiO_2$ | 64.37 | 64.86 | 64.34 | 65.11 | 64.84 | 65.23 | 65.26 | 64.14 | 64.04 | 63.01 |
| $B_2O_3$ | — | — | — | — | — | — | — | — | — | — |
| $Al_2O_3$ | 10.91 | 10.99 | 10.91 | 11.04 | 10.99 | 11.06 | 11.06 | 11.04 | 11.02 | 10.85 |
| MgO | 2.16 | 2.17 | 2.16 | 2.18 | 2.17 | 2.17 | 2.17 | 2.82 | 2.80 | 2.66 |
| CaO | 14.09 | 15.58 | 15.00 | 15.17 | 14.19 | 15.97 | 16.06 | 15.03 | 14.94 | 14.21 |
| SrO | 3.37 | — | — | — | — | — | — | — | — | — |
| BaO | — | 1.26 | 2.49 | — | — | — | — | — | — | — |
| ZnO | — | — | — | 1.34 | 2.67 | — | — | — | — | — |
| $Li_2O$ | 1.78 | 1.79 | 1.78 | 1.80 | 1.79 | 1.80 | 1.80 | 1.35 | 1.35 | — |
| $Na_2O$ | 2.85 | 2.87 | 2.85 | 2.89 | 2.87 | 2.89 | 2.89 | 4.78 | 4.78 | 7.45 |
| $K_2O$ | 0.47 | 0.48 | 0.47 | 0.48 | 0.48 | 0.48 | 0.48 | 0.54 | 0.54 | 0.53 |
| $Li_2O + Na_2O + K_2O$ | 5.10 | 5.14 | 5.10 | 5.17 | 5.14 | 5.17 | 5.17 | 6.67 | 6.67 | 7.98 |
| $TiO_2$ | — | — | — | — | — | — | 0.26 | 0.26 | 1.29 |
| $ZrO_2$ | — | — | — | — | — | 0.41 | — | — | — | — |
| $Fe_2O_3$ | — | — | — | — | — | — | 0.26 | 0.03 | 0.26 | — |
| Glass Transition Temperature [° C.] | 617 | 617 | 616 | 617 | 620 | 621 | 623 | 615 | 619 | 653 |
| Devitrification Temperature [° C.] | 1172 | 1188 | 1182 | 1171 | 1153 | 1188 | 1188 | 1188 | 1188 | 1215 |

TABLE 6-continued

| Component (mass %) or Physical Property | Ex. 51 | Ex. 52 | Ex. 53 | Ex. 54 | Ex. 55 | Ex. 56 | Ex. 57 | Ex. 58 | Ex. 59 | Ex. 60 |
|---|---|---|---|---|---|---|---|---|---|---|
| Working Temperature [° C.] | 1243 | 1238 | 1241 | 1247 | 1241 | 1243 | 1236 | 1229 | 1232 | 1264 |
| ΔT [° C.] | 71 | 50 | 59 | 76 | 88 | 55 | 48 | 41 | 44 | 49 |
| ΔW [mass %] | 0.19 | 0.17 | 0.18 | 0.12 | 0.09 | 0.16 | 0.15 | 0.28 | 0.26 | 0.44 |

TABLE 7

| Component (mass %) or Physical Property | Com. Ex. 1 | Com. Ex. 2 | Com. Ex. 3 | Com. Ex. 4 | Com. Ex. 5 | Com. Ex. 6 | Com. Ex. 7 | Com. Ex. 8 | Com. Ex. 9 | Com. Ex. 10 | Com. Ex. 11 |
|---|---|---|---|---|---|---|---|---|---|---|---|
| $SiO_2$ | 72.76 | 67.05 | 54.84 | 71.91 | 58.93 | 63.92 | 64.76 | 67.43 | 65.08 | 64.66 | 62.96 |
| $B_2O_3$ | — | 4.68 | 5.95 | — | — | — | — | — | — | — | — |
| $Al_2O_3$ | 1.88 | 4.02 | 14.52 | 11.02 | 11.18 | 15.77 | 9.24 | 9.62 | 8.38 | 9.22 | 8.98 |
| MgO | 3.58 | 2.58 | 0.38 | 1.87 | 3.19 | 2.11 | — | 10.54 | 0.86 | 0.82 | 2.21 |
| CaO | 7.62 | 6.53 | 22.80 | 10.05 | 21.48 | 13.13 | 19.34 | 5.47 | 16.15 | 15.44 | 15.73 |
| ZnO | — | 3.61 | — | — | — | — | — | — | — | — | — |
| $Li_2O$ | — | 0.59 | — | 1.80 | 1.82 | 1.77 | 0.32 | 0.33 | 9.54 | — | — |
| $Na_2O$ | 13.20 | 10.17 | 0.49 | 2.88 | 2.92 | 2.83 | 5.87 | 6.11 | — | 9.85 | — |
| $K_2O$ | 0.95 | 0.77 | 0.30 | 0.48 | 0.49 | 0.47 | 0.47 | 0.49 | — | — | 10.11 |
| $Li_2O + Na_2O + K_2O$ | 14.15 | 11.53 | 0.79 | 5.16 | 5.23 | 5.07 | 6.66 | 6.93 | 9.54 | 9.85 | 10.11 |
| $Fe_2O_3$ | — | — | 0.25 | — | — | — | — | — | — | — | — |
| F | — | — | 0.48 | — | — | — | — | — | — | — | — |
| Glass Transition Temperature [° C.] | 553 | 549 | 681 | 625 | 620 | 645 | 663 | 664 | 513 | 635 | 735 |
| Devitrification Temperature [° C.] | 1020 | 986 | 1090 | 1164 | 1220 | 1148 | 1312 | 1332 | 1071 | 1270 | 1337 |
| Working Temperature [° C.] | 1172 | 1165 | 1205 | 1382 | 1157 | 1307 | 1258 | 1327 | 1184 | 1244 | 1354 |
| ΔT [° C.] | 152 | 179 | 115 | 218 | −63 | 159 | −54 | −5 | 113 | −26 | 17 |
| ΔW [mass %] | 0.40 | 0.50 | 7.40 | 0.07 | 0.48 | 0.35 | 0.24 | 0.44 | 0.30 | 0.20 | 0.27 |

The transition temperatures of examples 1 to 60 were 584° C. to 683° C. This shows that these glasses have superior heat resistance capacities. The working temperatures of these glasses were 1214° C. to 1283° C. These are preferable temperatures for fabricating the glass flakes. Further, ΔT (working temperature–devitrification temperature) was 41° C. to 142° C. This is a temperature difference that does not cause devitrification in the fabrication process of the glass flakes 10. In these glasses, the mass decrease rate ΔW, which is the index of acid resistance, was 0.08 to 0.44 percent by mass. This shows that the glass flakes 10 have satisfactory acid resistance.

In contrast, the sheet glass composition of the prior art shown in comparative example 1 had a glass transition temperature of 553° C., which is low, and the heat resistance was poor.

The C glass of the prior art shown in comparative example 2 had a glass transition temperature of 549° C., which is lower that the glass transition temperatures of the glasses in examples 1 to 60, and the heat resistance was poor.

The E glass of the prior art shown in comparative example 3 had a mass decrease rate ΔW of 7.40 percent by mass, which is high, and the heat resistance was poor.

The working temperature of the glass in comparative example 4 was 1382° C., which is higher than the working temperature of the glasses of examples 1 to 60.

In the glass of comparative example 5, ΔT (working temperature–devitrification temperature) was −63° C. and smaller than the ΔT of the glasses of examples 1 to 60.

The working temperature of the glass in comparative example 6 was 1307° C., which is higher than the working temperature of the glasses of examples 1 to 60.

In the glass of comparative example 7, ΔT (working temperature–devitrification temperature) was −54° C. and smaller than the ΔT of the glasses of examples 1 to 60.

The working temperature of the glass in comparative example 8 was 1327° C., which is higher than the working temperature of the glasses of examples 1 to 60. Further, in this glass, ΔT (working temperature–devitrification temperature) was −5° C. and smaller than the ΔT of the glasses of examples 1 to 60.

The glass of comparative example 9 had a glass transition temperature of 513° C., which is much lower than the glass transition temperatures of the glasses in examples 1 to 60.

In the glass of comparative example 10, ΔT (working temperature–devitrification temperature) was −26° C. and smaller than the ΔT of the glasses of examples 1 to 60.

The glass of comparative example 11 had a glass transition temperature of 1354° C., which is higher than the glass transition temperatures of the glasses in examples 1 to 60.

In the above results, as in examples 1 to 60, the glasses of which silicon dioxide ($SiO_2$), aluminum oxide ($Al_2O_3$), alkali earth metal oxides (MgO, CaO), and alkali metal oxides ($Li_2O$, $Na_2O$, $K_2O$), which are within the range of the present invention, have superior heat resistance, chemical durability (acid resistance), and formability.

Then, the glasses of examples 1 to 60 and comparative example 10 were used to fabricate the glass flakes and the coated glass flakes. The glasses of each composition were melted again in the electrical furnace and then formed into pellets as they cooled. The pellets were fed to a fabrication apparatus shown in FIG. 1 to fabricate the glass flakes with an average thickness of 0.5 to 1 μm. An electronic microscope (Keyence Corporation, Real Surface View Microscope, VE-7800) was used to measure the thickness of glass flake from cross-sections of 100 glass flakes and obtain the average thickness of the glass flakes.

EXAMPLES 61 TO 120

From the glass flakes having the compositions of examples 1 to 60 fabricated in this manner, the coated glass flakes 12 of examples 61 to 120 were fabricated through the procedures described below. First, the glass flakes were crushed into a predetermined grain diameter. Then, liquid phase processing was performed to cover the surface of the glass flakes with titanium dioxide. The liquid phase deposits titanium dioxide from metal salts onto the surface of the glass flakes 10. More specifically, stannous chloride dihydrate serving as a metal salt was dissolved in ion-exchanged water and diluted hydrochloric acid was added for adjustment to pH 2.0 to 2.5. The glass flakes 10 were added to the solution while being agitated and then filtered after ten minutes. Subsequently, chloroplatinic acid hexahydrate was dissolved in the ion exchanged water and the filtered glass flakes 10 were added while being agitated and filtered after ten minutes. Then, a hydrochloric acid solution (35 percent by mass) was added to the ion exchanged water to obtain an acid solution of hydrochloric acid having pH 0.7. The glass flakes 10 were added to the acid solution while being agitated, and the solution temperature was heated to 75° C.

Further, titanium tetrachloride ($TiCl_4$) solution was added to the above solution at a rate of 0.2 g/min in titanium equivalent. At the same time, sodium hydroxide was added so as not to change the pH. Through a neutralization reaction, titanium dioxide ($TiO_2$) or its hydrate was deposited on the surface of the glass flakes 10 for two hours. Then, the glass flakes 10 on which the coatings 11 were formed were filtered and dried for two hours at 180° C. The coated glass flakes 12 fabricated in this manner were observed with an electronic microscope, and the formation of the coatings 11 of titanium oxide on the surfaces of the glass flakes 10 was confirmed.

EXAMPLES 121 TO 180

From the glass flakes having the compositions of examples 1 to 60, the coated glass flakes 12 of examples 121 to 180 were fabricated through the procedures described below. First, the glass flakes were crushed into a suitable grain diameter. Then, the surfaces of the glass flakes were coated with silver by performing conventional electroless plating. The conventional electroless plating will now be described. First, a pre-processing using stannous chloride and chloroplatinic acid hexahydrate were performed in the same manner as in examples 61 to 120 on the glass flakes 10. Then, 200 g of silver nitrate and a suitable amount of ammonia water were added to 10 L of ion exchanged water to prepare a silver liquid. Then, 1 kg of glass flakes that have undergone the preprocessing were added to the silver liquid while being agitated. Further, 14 percent by mass of sodium-potassium tartrate solution was added as a reduction liquid, and the surface of the glass flakes 10 were coated with silver. Afterwards, the glass flakes 10 were filtered and dried for two hours at 400° C. The coated glass flakes 12 that have coatings 11 of silver on the surfaces of the glass flakes 10 were obtained in this manner.

The coated glass flakes 12 fabricated in this manner were observed with an electronic microscope, and the formation of the coatings 11 of silver on the surfaces of the glass flakes 10 was confirmed.

EXAMPLES 181 TO 240 AND COMPARATIVE EXAMPLE 12

First, the glass flakes having the compositions of examples 1 to 60 were crushed to predetermined grain diameters and then mixed with a polyester resin to obtain the polyester resin compositions of examples 181 to 240 containing the glass flakes 10. The polyester resin compositions had satisfactory dispersibility in the glass flakes 10 and achieved a satisfactory outer appearance.

In contrast, in comparative example 12, the glass flakes 10 having the composition of comparative example 12 were crushed to predetermined grain diameters and 5 and then mixed with polyester resin. As a result, the glass flakes 10 of comparative example 10 were devitrificated. Thus, the outer appearance of the polyester resin composition was not preferable.

EXAMPLES 241 TO 300

The coated glass flakes 12 of examples 61 to 120 were mixed with epoxy acrylate to obtain the vinyl ester paints of examples 241 to 300 containing the coated glass flakes 12. The vinyl ester paints had satisfactory dispersibility in the glass flakes 10 and achieved a satisfactory outer appearance.

EXAMPLES 301 TO 360

The coated glass flakes 12 of examples 61 to 120 were mixed with a foundation, which is a facial cosmetic, to obtain the cosmetics of examples 301 to 360 containing the coated glass flakes 12. The cosmetics had satisfactory dispersibility in the coated glass flakes 12, which was satisfactory for cosmetics.

EXAMPLES 361 TO 420

The coated glass flakes 12 of examples 61 to 120 were mixed with ink compositions, in which a coloring agent, a resin, and an organic solvent were mixed in predetermined amounts, to obtain the ink compositions of examples 361 to 420 containing the coated glass flakes 12. The ink compositions had satisfactory dispersibility in the glass flakes 10, which was satisfactory as ink compositions.

The above-discussed embodiment may be modified as described below.

As the composition of the glass base material, the range of $SiO_2+Al_2O_3$ may be specified, and the range for the components forming the glass skeleton may be clarified.

As the alkali metal oxides ($Li_2O+Na_2O+K_2O$), cesium oxide ($Ce_2O$), rubidium oxide ($Rb_2O$), and the like, which are oxides of univalent alkali metals may be added.

As the composition of the glass base material, among the alkali metal oxides $Li_2O$, $Na_2O$, and $K_2O$, the ranges of two components or one component may be clarified.

The glass flake 10 may have other cross-sectional shapes in the thicknesswise direction. For example, the two principal surfaces may be parallel to each other. Alternatively, the two principal surfaces may be inclined to one another (tapered).

Technical features that can be recognized from the above-discussed embodiment will now be described.

The glass base material is set to satisfy $50 \leq (SiO_2-Al_2O_3) \leq 60$. In such a case, the acid resistance of the glass flakes is increased.

The working temperature of the glass base material is 1100° C. to 1300° C. In this case, in addition to the advantages of the invention according to any one of claims 1 to 4, the workability when forming the glass flakes is increased.

The metal that is the main component in the coating of the coated glass flake is at least one selected from the group consisting of nickel, gold, solver, platinum, and palladium.

The metal oxide that is the main component in the coating of the coated glass flake is at least one selected from the group consisting of titanium oxide, iron oxide, cobalt oxide, zirconium oxide, zinc oxide, tin oxide, and silicon oxide.

A resin composition being characterized by containing the glass flakes or the coated glass flakes. This obtains a resin molded product having physical properties that increase the strength, dimensional accuracy, and the like.

A paint being characterized by containing the glass flakes or the coated glass flakes. This adds a metallic color or luster to a paint film formed from the paint.

An ink composition being characterized by containing the glass flakes or the coated glass flakes. This adds a metallic color or luster to characters, drawings, and the like formed from the ink composition.

Cosmetics being characterized by containing the glass flakes or the coated glass flakes. This adds a color tone or luster after the cosmetics is applied to the face or the like.

The invention claimed is:

1. A glass flake being characterized in that the glass flake is formed from a glass base material comprising, expressed in percent by mass:
   $63 \leq SiO_2 \leq 70$;
   $10.85 \leq Al_2O_3 \leq 15$;
   $1 \leq MgO \leq 10$;
   $10 \leq CaO \leq 17.77$;
   $4.08 \leq (Li_2O+Na_2O+K_2O) < 9$; and
   $0 \leq Fe_2O_3 \leq 5$,
   wherein the content of $Li_2O$ is 1.30 percent by mass or greater and ZnO is substantially not contained,
   wherein a temperature difference $\Delta T$ obtained by subtracting a devitrification temperature from a working temperature of the glass base material, which is the temperature when the viscosity of molten glass is 100 Pa·sec (1000 P), is 0° C. to 200° C.,
   wherein a glass transition temperature of the glass base material is 560° C. to 750° C., and
   wherein $\Delta W$, which is a mass decrease rate measured by immersing the glass base material in a sulfuric acid aqueous solution for 72 hours at 80° C. and representing an index for acid resistance of the glass base material, is 0.05 to 1.2 percent by mass.

2. A coated glass flake being characterized by:
   the glass flake according to claim 1, and
   a coating that covers a surface of the glass flake, the coating having a main component of metal or metal oxide.

3. The glass flake according to claim 1, being characterized in that SrO, BaO and $ZrO_2$ are substantially not contained.

4. The glass flake according to claim 1, being characterized in that the lower limit of CaO is greater than 15 percent by mass.

5. The glass flake according to claim 1, being characterized by $0 \leq B_2O_3 < 2$.

6. The glass flake according to claim 1, being characterized by $4.17 \leq (Li_2O+Na_2O+K_2O) < 9$.

7. The glass flake according to claim 1, being characterized by $4.5 \leq (Li_2O+Na_2O+K_2O) < 9$.

8. A method for fabricating the glass flake according to claim 1, comprising:
   melting a glass base material comprising, expressed in percent by mass:
   $63 \leq SiO_2 \leq 70$;
   $10.85 \leq Al_2O_3 \leq 15$;
   $1 \leq MgO \leq 10$;
   $10 \leq CaO \leq 17.77$;
   $4.08 \leq (Li_2O+Na_2O+K_2O) < 9$; and
   $0 \leq Fe2O3 \leq 5$,
   wherein the content of $Li_2O$ is 1.30 percent by mass or greater and ZnO is substantially not contained,
   wherein a temperature difference $\Delta T$ obtained by subtracting a devitrification temperature from a working temperature of the glass base material, which is the temperature when the viscosity of molten glass is 100 Pa·sec (1000 P), is 0° C. to 200° C.,
   wherein a glass transition temperature of the glass base material is 560° C. to 750° C., and
   wherein $\Delta W$, which is a mass decrease rate measured by immersing the glass base material in a sulfuric acid aqueous solution for 72 hours at 80° C. and representing an index for acid resistance of the glass base material, is 0.05 to 1.2 percent by mass; and
   then crushing the glass base material.

9. A glass base material for forming the glass flake according to claim 1, the glass base material comprising, expressed in percent by mass:
   $63 \leq SiO_2 \leq 70$;
   $10.85 \leq Al_2O_3 \leq 15$;
   $1 \leq MgO \leq 10$;
   $10 \leq CaO \leq 17.77$;
   $4.08 \leq (Li_2O+Na_2O+K_2O) < 9$; and
   $0 \leq Fe_2O_3 \leq 5$,
   wherein the content of $Li_2O$ is 1.30 percent by mass or greater and ZnO is substantially not contained,
   wherein a temperature difference $\Delta T$ obtained by subtracting a devitrification temperature from a working temperature of the glass base material, which is the temperature when the viscosity of molten glass is 100 Pa·sec (1000 P), is 0° C. to 200° C.,
   wherein a glass transition temperature of the glass base material is 560° C. to 750° C., and
   wherein $\Delta W$, which is a mass decrease rate measured by immersing the glass base material in a sulfuric acid aqueous solution for 72 hours at 80° C. and representing an index for acid resistance of the glass base material, is 0.05 to 1.2 percent by mass.

* * * * *